(12) United States Patent
Van Valkenburgh et al.

(10) Patent No.: US 8,956,146 B2
(45) Date of Patent: Feb. 17, 2015

(54) APPARATUS FOR EMBOSSING A WEB

(71) Applicant: The Procter & Gamble Company, Cincinnati, OH (US)

(72) Inventors: Curtis Hunter Van Valkenburgh, Mason, OH (US); Richard George Coe, Cincinnati, OH (US); Keith Joseph Stone, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/850,701

(22) Filed: Mar. 26, 2013

(65) Prior Publication Data
US 2013/0209599 A1   Aug. 15, 2013

Related U.S. Application Data

(63) Continuation of application No. 13/045,991, filed on Mar. 11, 2011.

(51) Int. Cl.
B29C 59/04 (2006.01)
A61F 13/15 (2006.01)
B29C 59/02 (2006.01)

(52) U.S. Cl.
CPC ........... B29C 59/04 (2013.01); A61F 13/15707 (2013.01); B29C 59/022 (2013.01); B29C 2791/007 (2013.01)
USPC ............ 425/405.1; 425/326.1; 425/356; 425/362; 425/374

(58) Field of Classification Search
USPC ............ 425/374, 326.1, 356, 362, 405.1
See application file for complete search history.

(56) References Cited

U.S. PATENT DOCUMENTS

| | | | | |
|---|---|---|---|---|
| 3,227,854 A | * | 1/1966 | Ramsey et al. | 219/244 |
| 3,700,523 A | * | 10/1972 | Sato | 156/210 |
| 4,161,383 A | | 7/1979 | Gadani | |
| 4,319,868 A | * | 3/1982 | Riemersma et al. | 425/290 |
| 5,030,081 A | * | 7/1991 | Schulz | 425/363 |
| 5,145,549 A | * | 9/1992 | Mosburger | 156/382 |
| 5,441,691 A | | 8/1995 | Dobrin et al. | |
| 5,972,280 A | * | 10/1999 | Hoagland | 264/555 |
| 6,082,292 A | * | 7/2000 | Denes et al. | 118/718 |
| 6,251,207 B1 | * | 6/2001 | Schultz et al. | 156/209 |
| 6,257,866 B1 | * | 7/2001 | Fritz et al. | 425/387.1 |
| 6,287,427 B1 | * | 9/2001 | Beck | 162/360.3 |
| 6,780,372 B2 | * | 8/2004 | Gray | 264/504 |
| 7,857,027 B2 | | 12/2010 | Nitta | |
| 2002/0125606 A1 | * | 9/2002 | McGuire et al. | 264/167 |
| 2010/0230858 A1 | | 9/2010 | Stone et al. | |
| 2010/0230866 A1 | | 9/2010 | Gray et al. | |
| 2010/0230867 A1 | | 9/2010 | Gray et al. | |

FOREIGN PATENT DOCUMENTS

WO    2009157785 A1    12/2009

OTHER PUBLICATIONS

PCT International Search Report PCT/US2011/028084, dated Jul. 4, 2011, 11 pages.

* cited by examiner

*Primary Examiner* — Amjad Abraham
(74) *Attorney, Agent, or Firm* — Andres E. Velarde

(57) ABSTRACT

An apparatus for embossing a web having a static gas pressure plenum and a forming structure disposed in contact to the static gas pressure plenum. The static gas pressure plenum provides a static gas pressure of from about 0.1 MPa to about 25 MPa.

7 Claims, 7 Drawing Sheets

APPARATUS FOR EMBOSSING A WEB

CROSS REFERENCE TO RELATED APPLICATION(S)

This application claims the benefit of U.S. patent application Ser. No. 13/045,991 which claims the benefit of U.S. Provisional Application No. 61/313,122, filed Mar. 11, 2010. All documents are incorporated herein by reference.

FIELD OF THE INVENTION

The present invention relates to an apparatus for embossing a web.

BACKGROUND OF THE INVENTION

Web materials, such as thermoplastic films, have a variety of uses including component materials of absorbent articles (such as topsheets and backsheets), packaging (such as flow wrap, shrink wrap, and polybags), trash bags, food wrap, dental floss, wipes, electronic components, and the like. For many of these uses of web materials, it can be beneficial for the web material to have a textured surface, which can provide the surface of the web material with a desirable feel, visual impression, and/or audible impression.

Polymeric webs exhibiting a soft and silky tactile impression can be made via a vacuum forming process or a hydroforming process. With a typical vacuum forming process, a precursor web is heated and placed over a forming structure. Then a vacuum forces the precursor web to conform to the texture of the forming structure. The resulting polymeric web has texture that can provide a soft and silky tactile impression, depending upon the texture of the forming structure and degree of conformation. While a vacuum forming process can be suitable for making a soft and silky polymeric web, a vacuum forming process is typically limited with respect to the amount of pressure capable of being exerted onto a precursor web. As a result, it is usually required to heat a precursor film to significantly soften or melt the precursor film prior to placement on the forming structure in order to vacuum form the precursor film to the forming structure. A vacuum forming process is therefore an inefficient process in terms of how fast the process can be performed due to the heating step and the limited pressures generated by the process.

With a typical hydroforming process, a precursor web is placed over a forming structure and high pressure and high temperature water jets force the precursor web to conform to the texture of the forming structure. The resulting polymeric web can have texture that can provide a soft and silky tactile impression, depending upon the texture of the forming structure. A hydroforming process, although capable of producing soft and silky polymeric webs, is typically a costly and inefficient process involving the use of high pressure and high temperature water jets and subsequent drying steps, including dewatering steps.

Embossing is a process that typically involves the act of mechanically working a substrate to cause the substrate to conform under pressure to the depths and contours of a pattern engraved or otherwise formed on an embossing roll. It is widely used in the production of consumer goods. Manufacturers use the embossing process to impart a texture or relief pattern into products made of textiles, paper, synthetic materials, plastic materials, metals, and wood. When the substrate is a thermoplastic, permanent strain remaining in the substrate can provide a texture and/or visual that remains with the surface of the substrate.

Embossing processes have been used to provide texture to polymeric films. However, such embossing processes typically require extruding a molten resin onto a forming structure or heating a precursor web before placement onto a forming structure and then embossing to produce an embossed web. The embossed web is then cooled, typically by cooling the embossing rolls or plates used to emboss the heated precursor web or molten resin. The cooling step is often utilized to set the texture in the embossed web. However, these heating and cooling steps add undesirable cost and inefficiency, as well as complexity, to the process. In addition, such embossing processes typically involve relatively large dwell times, which can result in slow, inefficient processes.

It is also typically difficult to impart relatively small scale texture to precursor webs using conventional embossing processes. Furthermore, typical embossing processes tend to produce embossed webs having relatively uniform thickness throughout the web.

Despite the knowledge in the art, there remains a desire to develop a more efficient and effective apparatus for making embossed webs.

SUMMARY OF THE INVENTION

The present invention relates to an apparatus for embossing a web comprising an area containing a static gas pressure plenum and one or more forming structures. The static gas pressure plenum provides a static gas pressure of from about 0.1 MPa to about 25 MPa.

The present invention also relates to an apparatus for embossing a web comprising a pressure hood, a forming structure disposed adjacent said pressure hood, a gap between said pressure hood and said forming structure defining a static gas pressure plenum, an infeed sealing roller contacting said forming structure, thereby forming an infeed nip, and an outfeed sealing roller contacting said forming structure, thereby forming an outfeed nip.

The present invention also relates to an apparatus for embossing a web comprising one or more compliant rolls and one or more forming structures. The one or more forming structures and the one or more compliant rolls are in contact forming a high pressure zone defining a static gas pressure plenum.

DETAILED DESCRIPTION OF THE INVENTION

Figure 1:
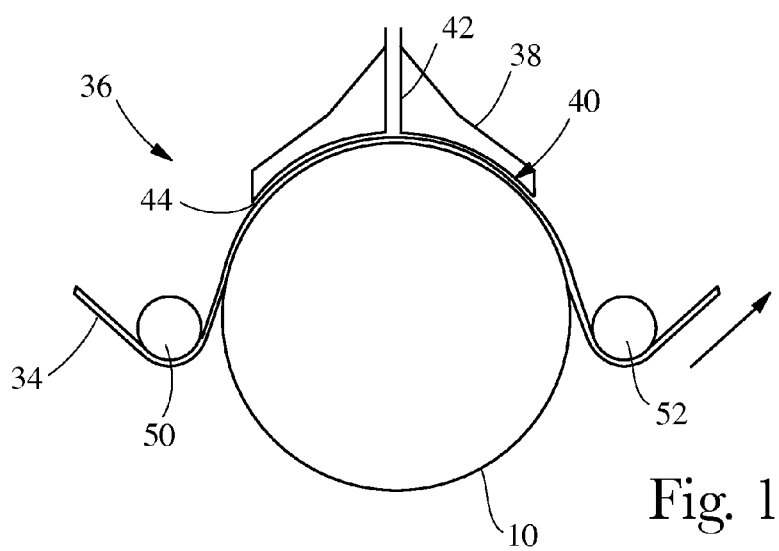
FIG. 1 is a schematic of an apparatus for embossing a web in accordance with an embodiment of the disclosure.

The apparatus 36 of the present invention is utilized to emboss a precursor web 34 of material in order to impart a texture and/or pattern into the web of material. The apparatus 36 of the present invention includes a forming structure 10 and a static gas pressure plenum 40. The static gas pressure plenum 40 may be formed by a pressure hood 38 or by one or more forming structures 10 and one or more compliant rolls 80 in contact enclosing a high pressure zone 46.

The apparatus 36 as shown in FIG. 1 includes a forming structure 10, an infeed 50 and outfeed 52 sealing roller, and a pressure hood 38. The forming structure 10 can be any suitable forming structure 10 designed to impart a texture and/or pattern into a precursor web 34 of material to form an embossed web. The pressure hood 38 includes a high pressure gas inlet 42. The gap 44 between the forming structure 10 and the pressure hood 38 defines a static gas pressure plenum 40.

Figure 2:
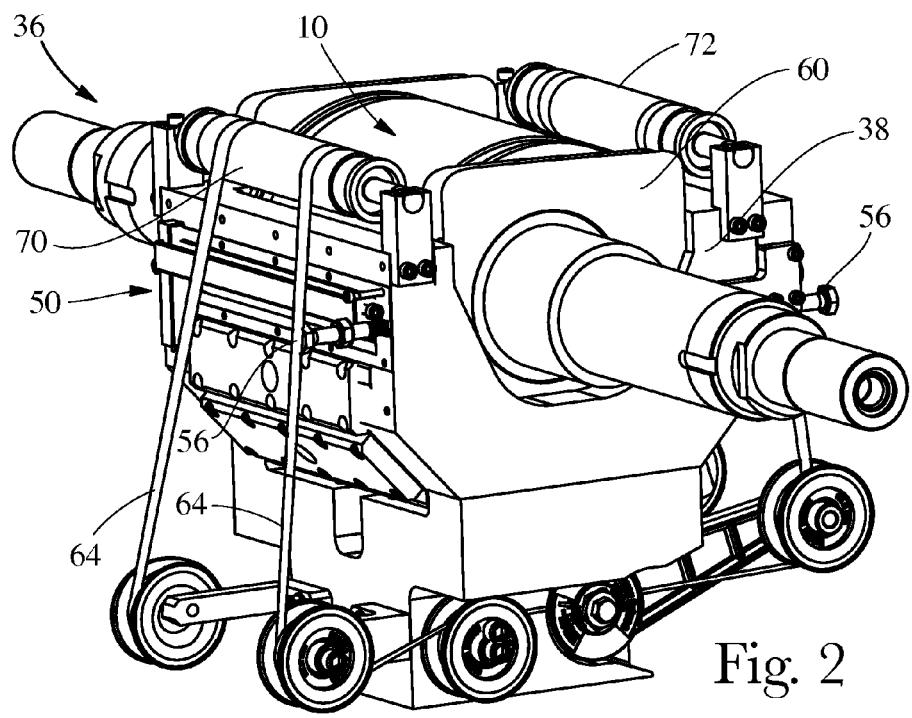
FIG. 2 is a perspective view of an apparatus for embossing a web in accordance with an embodiment of the disclosure mounted in a frame with a side plate of the frame removed.

The apparatus 36 as shown in FIG. 2 includes a forming structure 10, an infeed sealing roller 50, idler rolls 70, 72, web sealing belts 64, spring loaded mounts 56, a sealing plate 60, and a pressure hood 38.

Figure 3:
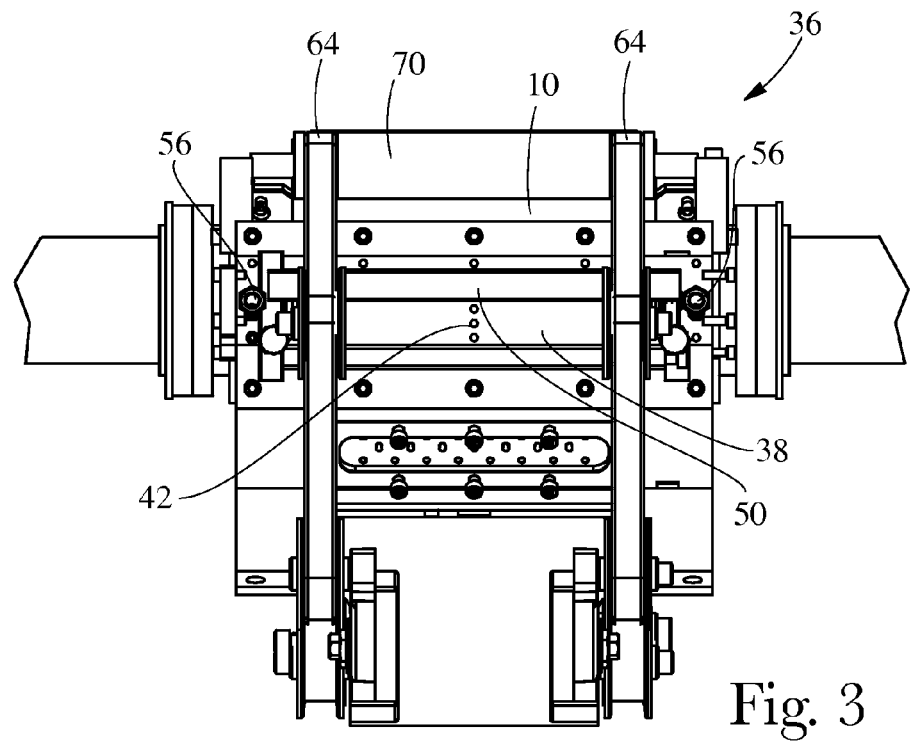
FIG. 3 is a side view of an apparatus for embossing a web in accordance with an embodiment of the disclosure.

The apparatus 36 as shown in FIG. 3 includes a forming structure 10, a pressure hood 38, an infeed sealing roller 50, spring loaded mounts 56, web sealing belts 64, an idler rolls 70, and a high pressure gas inlet 42 located in the pressure hood 38. The high pressure gas inlet 42 provides a static gas pressure of from about 0.1 MPa to about 25 MPa to the static gas pressure plenum 40.

Figure 4:
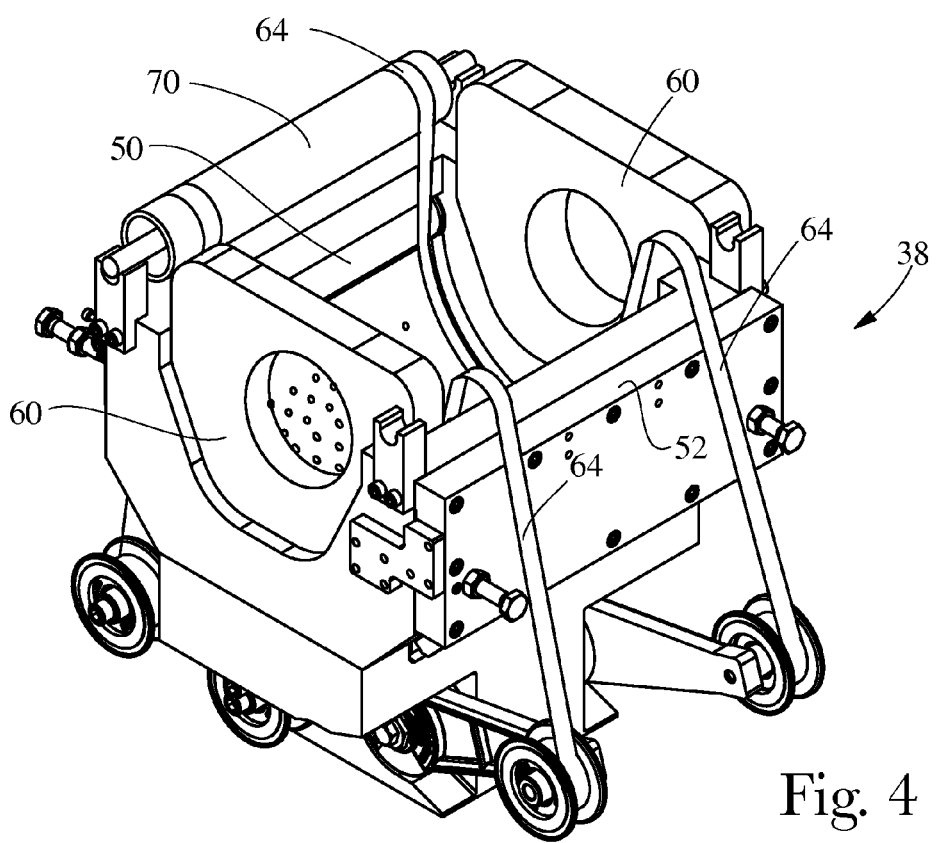
FIG. 4 is a perspective view of a pressure hood of an apparatus for embossing a web with the forming structure and one infeed idler roll removed in accordance with an embodiment of the disclosure with the forming structure roll removed.

The pressure hood 38 as shown in FIG. 4 includes infeed 50 and outfeed 52 sealing rollers, web sealing belts 64, an idler roll 70, and sealing plates 60.

Figure 5:
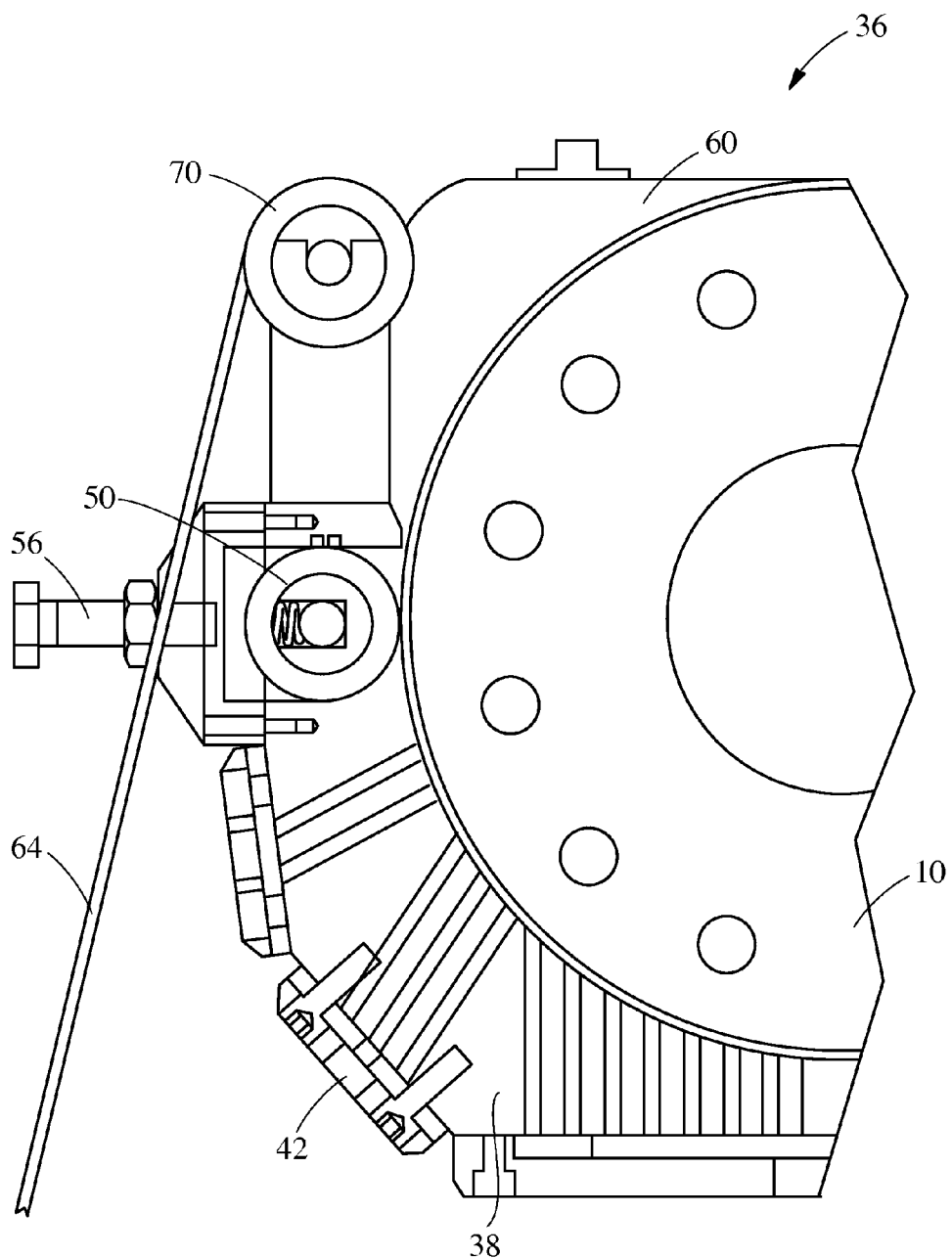
FIG. 5 is a cross-sectional view of an apparatus for embossing a web in accordance with an embodiment of the disclosure.

The apparatus 36 as shown in FIG. 5 includes a forming structure 10, a pressure hood 38, a high pressure gas inlet 42, an infeed sealing roller 50, a spring loaded mount 56 that impacts upon the infeed sealing roller 50, a web sealing belt 64, and an idler roll 70.

Figure 6:
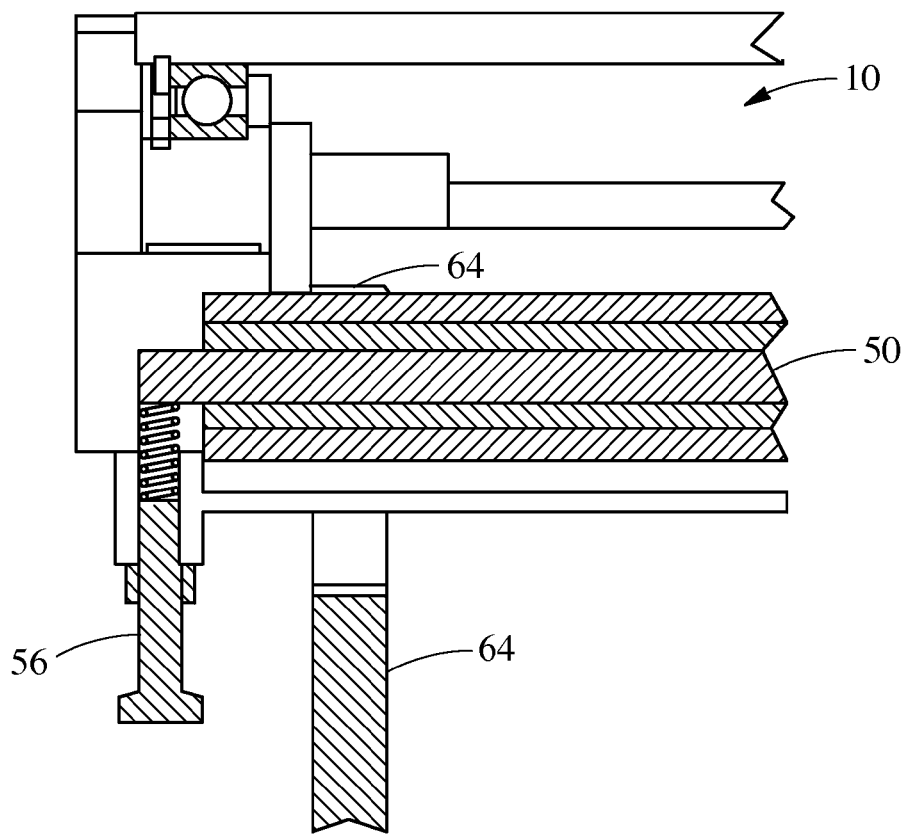
FIG. 6 is a cross-sectional view of a sealing roller and forming structure interface of an apparatus for embossing a web in accordance with an embodiment of the disclosure.

The apparatus 36 as shown in FIG. 6 represents a cross-sectional view of a sealing roller 50 and forming structure 10 interface. The cross sectional view includes a spring loaded mount 56 and a web sealing belt 64.

Figure 7:
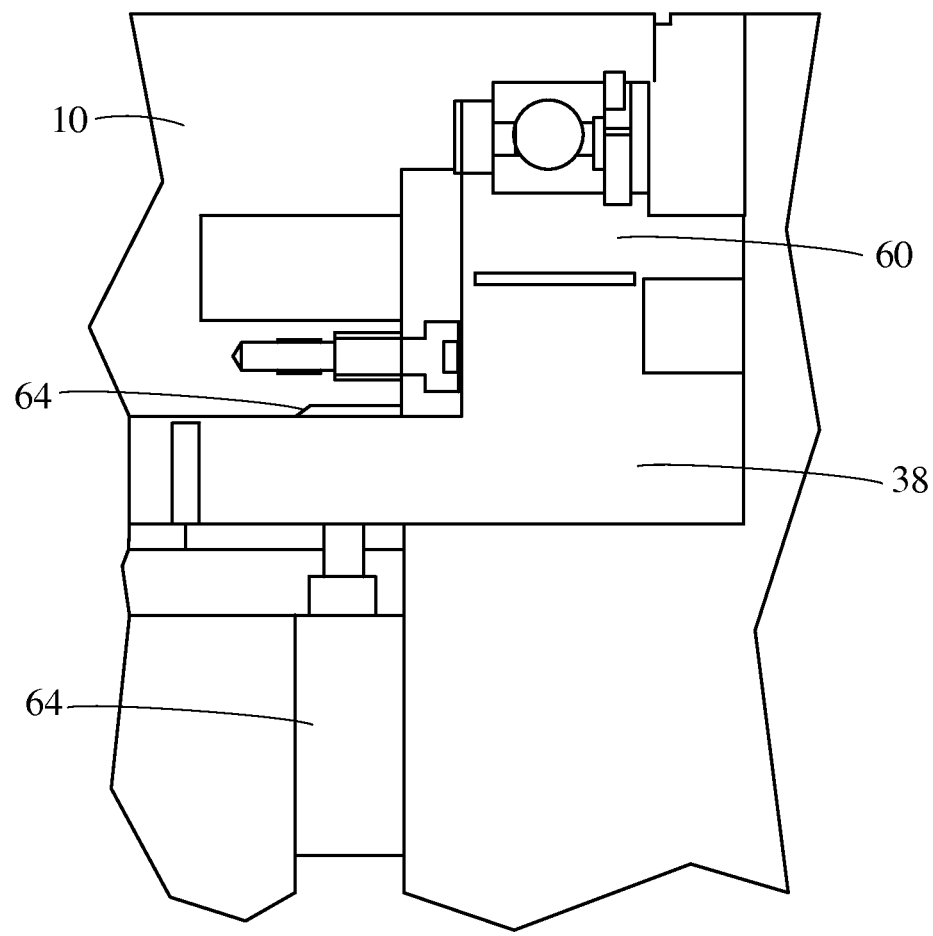
FIG. 7 is a cross-sectional view of a forming structure, pressure hood, and stationary sealing plate of an apparatus for embossing a web in accordance with an embodiment of the disclosure.

The apparatus 36 as shown in FIG. 7 represents a cross-sectional view of a forming structure 10, a pressure hood 38, and a stationary sealing plate 60. The cross-sectional view includes a web sealing belt 64.

Figure 8:
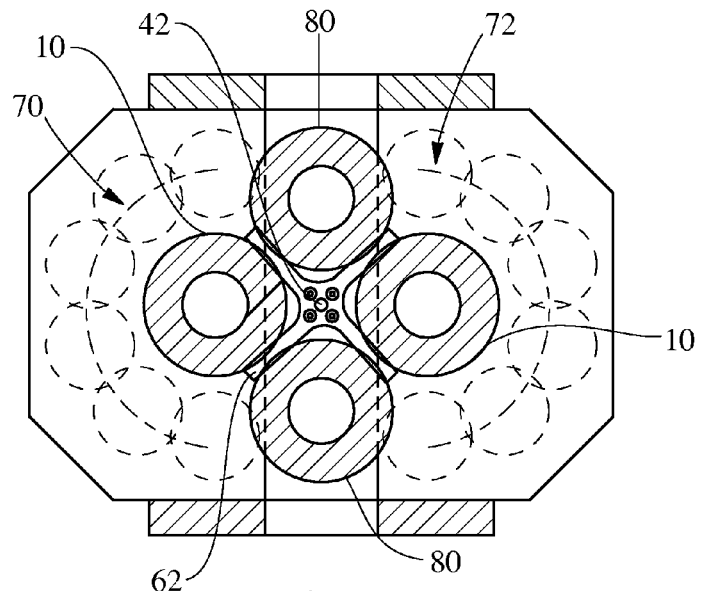
FIG. 8 is a schematic of an apparatus for embossing a web in accordance with an embodiment of the disclosure.

The schematic as shown in FIG. 8 represents an embodiment including two forming structures 10, two compliant rolls 80, a framing plate 62, a high pressure gas inlet 42 that provides a static gas pressure of from about 0.1 MPa to about 25 MPa to the static gas pressure plenum 40, and inlet and outlet idler rolls 70, 72.

Figure 9:
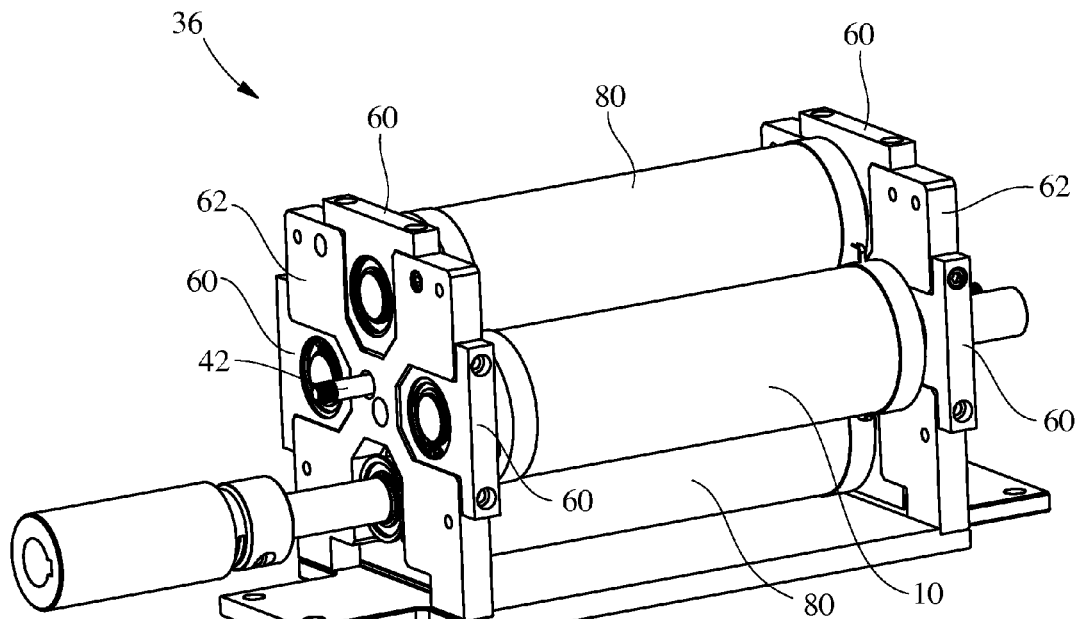
FIG. 9 is a perspective view of an apparatus for embossing a web in accordance with an embodiment of the disclosure.

The apparatus 36 as shown in FIG. 9 includes two forming structure 10, two compliant rolls 80, eight sealing plates 60, two framing plates 62, and a high pressure gas inlet 42.

Figure 10:
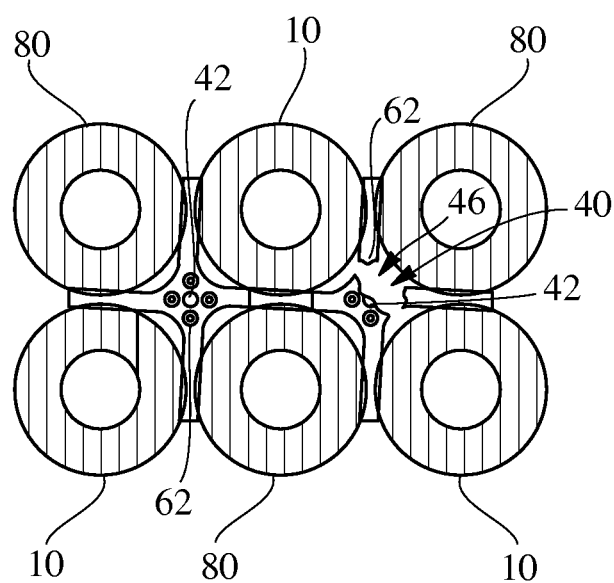
FIG. 10 is a schematic of an apparatus for embossing a web in accordance with an embodiment of the disclosure.

The schematic as shown in FIG. 10 represents an embodiment including three forming structures 10, three compliant rolls 80, two framing plates 62, two high pressure gas inlets 42 that provide static gas pressure of from about 0.1 MPa to about 25 MPa to each static gas pressure plenum 40. The forming structures 10 may differ in pattern and material. The two high pressure gas inlets 42 can provide different pressures between 0.1 MPa to about 25 MPa to each static gas pressure plenum 40 such that the pressures vary in each high pressure zone 46.

The forming structure 10 can be any suitable forming structure 10 designed to impart a texture and/or pattern into a precursor web 34 of material to form an embossed web. The forming structures 10 are typically in the form of a roll or sleeve. In an embodiment, forming structure 10 is in the form of a belt. The forming structure 10 may be made from any suitable material, such as, for example, aluminum, nickel, copper, low carbon steel, stainless steel, or tungsten carbide. The forming structure 10 can also be made from plastics, such as, for example, Delrin (Acetal Resin), Lexan, Nylon, PVC, or any other plastic that exhibits high stiffness, low friction, good dimensional stability, and is machinable.

In one embodiment, the forming structure 10 comprises a plurality of discrete apertures, discrete depressions, or combinations thereof. Such a forming structure 10 is described in more detail in U.S. Publication No. 2010-0230866 A1, filed Mar. 11, 2010.

In one embodiment, the forming structure 10 comprises a plurality of discrete protruded elements. Such a forming structure 10 is described in more detail in U.S. Publication No. 2010-0230867 A1, filed Mar. 11, 2010.

In one embodiment, the forming structure 10 comprises a plurality of discrete apertures, discrete depressions, discrete protruded elements or combinations thereof.

In an embodiment, the compliant rolls 80 are made of urethane. Alternatively, the compliant rolls 80 may be made of any suitable material, such as, for example, polyurethane, natural rubber, and gum rubber. The compliant rolls 80 may also vary in diameter. Other suitable compliant materials are described in more detail in U.S. Publication No. 2010-0230858 A1, filed Mar. 11, 2010.

A high pressure gas inlet 42 provides a source of high pressure gas to the static gas pressure plenum 40. The gas can be air, nitrogen, carbon dioxide, and the like, or combinations thereof. The static gas pressure plenum 40 exerts a pressure on the precursor web 34. Under static gas pressure conditions, there is no velocity and density impinging upon the unembossed precursor web 34 as with a velocity pressure source such as an air knife. Rather, a static high gas pressure is maintained which creates a pressure differential across the precursor web, between the static gas pressure plenum 40 facing surface of the precursor web 34 and the forming structure 10 facing surface of the precursor web 34.

A pressure of about 100 psi is provided by the static gas pressure plenum 40. The pressure is sufficient to force the precursor web 34, which is positioned between the forming structure 10 and static gas pressure plenum 40, into the discrete apertures or depressions, or about the discrete protruded elements, of the forming structure 10 to form an embossed web. In general, the pressure provided between the forming structure 10 and static gas pressure plenum 40 is about 0.1 MPa to about 25 MPa, about 1 MPa to about 20 MPa, about 0.5 MPa to about 10 MPa, about 7 MPa to about 25 MPa, about 10 MPa to about 25 MPa, or about 0.5 MPa to about 5 MPa.

The pressure provided by the static gas pressure plenum 40 allows for improved dwell times of the precursor web 34 on the forming structure 10. In an embodiment, the pressure is typically applied to the precursor web 34 for a dwell time of less than about 5 seconds, less than about 1 second, less than about 0.5 second, less than about 0.1 second, less than about 0.01 second, or less than about 0.005 second. For example, the dwell time can be about 0.5 milliseconds to about 50 milliseconds. Even with such relatively short dwell times, embossed webs can be produced with desirable structural features described herein. As a result, the process of the disclosure enables high speed production of embossed webs.

The precursor web 34 can be fed between the forming structure 10 and the static gas pressure plenum 40 at a rate of at least about 0.01 meters per second, at least about 1 meter per second, at least about 5 meters per second, or at least about 10 meters per second. Other suitable rates include, for example, at least about 0.01, 0.05, 0.1, 0.5, 1, 2, 3, 4, 5, 6, 7, 8, 9, or 10 meters per second.

The apparatus 36 can further include a sealing plate 60 disposed on each end of the forming structure roll 10 and compliant roll 80. The sealing plate 60 is a stationary member that maintains a lateral seal against the edges of the forming structure roll 10 and compliant roll 80.

The apparatus can further comprise infeed 70 and outfeed 72 idler rollers. In an embodiment, the infeed 70 and outfeed 72 idler rollers are adjustable in relation to the forming structure.

Web sealing belts 64 can be included to seal the sides of the precursor web 34 against the forming structure 10 as it enters the infeed nip, and as it exits the outfeed nip, to ensure that a pressure difference across the web is maintained so that the high pressure gas can impact the web. Web sealing belts 64 can also be included to seal the sides of the precursor web 34 against the one or more forming structures 10 when the high pressure zone 46 is defined by one or more forming structures 10 and one or more compliant rolls 80.

The web sealing belts 64 can fit into recessed areas at each end of the infeed 70 and outfeed 72 idler rolls, as shown in FIGS. 3 and 4. The web sealing belts 64 can further fit into recessed areas at each end of the forming structure roll 10 as shown in FIGS. 6 and 7.

In an embodiment, vacuum can be used on the forming structure 10. The vacuum can aid in removing trapped air under the web and avoiding pneumatic pressure under the web as the film is conformed to the forming structure 10. The vacuum can enhance the pressure differential across the web. The vacuum can be applied in any suitable manner, such as, for example, by using vent holes that are smaller in diameter than the thickness of the precursor web 34 or by using apertures. Alternatively, the vacuum can also be applied by using a porous forming structure 10. In an embodiment, vacuum can be applied inside a forming structure 10.

In an embodiment, heat is used during the embossing process. Heat can be provided in any suitable manner, such as, for example, by heating the high pressure gas, heating the forming structure 10, pre-heating the precursor web 34, heating the compliant rolls 80, using localized heat such as, for example, inserting a small cartridge heater inside the forming structure 10, or radiant heat as described in Gray (U.S. Pat. No. 6,780,372). Heat can also be provided by any combination of the sources that provide heat.

The precursor web 34 that is embossed by the apparatus of the present invention can be comprised of a wide variety of materials. Suitable precursor webs 34 include synthetic material, metallic material, biological material (in particular, animal-derived material), or combinations thereof. In one embodiment, the precursor web 34 is a thermoplastic film, preferably comprised of polyethylene, polypropylene, or blends thereof. Other suitable precursor webs are described in detail in U.S. Publication No. 2010-0230866 A1, filed Mar. 11, 2010 and U.S. Publication No. 2010-0230867 A1, filed Mar. 11, 2010.

The apparatus 36 of the present invention can be utilized in processes for making embossed webs, such as those processes described in detail in U.S. Publication No. 2010-0230866 A1, filed Mar. 11, 2010 and U.S. Publication No. 2010-0230867 A1, filed Mar. 11, 2010.

An embodiment of the apparatus 36 can further include infeed 50 and outfeed 52 sealing rollers which each contact the forming structure to define an infeed nip and an outfeed nip. The infeed 50 and outfeed 52 sealing rollers are utilized to enhance the seal of the static gas pressure plenum 40 to maintain sufficient gas pressure in the static gas pressure plenum 40 and also minimize air leakage.

In an embodiment, the infeed 50 and outfeed 52 sealing rollers can also be utilized to further force the precursor web 34 against the forming structure 10 in order to enhance the formation of texture and/or pattern in the embossed web and also minimize air leakage. Spring-loaded mounts 56 or other similar mounts can be utilized to further force the infeed 50 and/or outfeed 52 sealing rollers against the forming structure 10 in order to increase the amount of pressure applied to the precursor web 34 as it enters the infeed nip or outfeed nip. To enhance the formation of texture and/or pattern in the embossed webs, the infeed nip and/or outfeed nip can exhibit pressures ranging from about 0.3 MPa to about 68.9 MPa, from about 0.7 MPa to about 34.5 MPa, or from about 0.7 MPa to about 24.1 MPa.

The infeed 50 and/or outfeed 52 sealing rollers can comprise a compliant material. Suitable compliant materials include elastomers, felts, liquid-filled bladders, and combinations thereof. Other suitable compliant materials are described in detail in U.S. Publication No. 2010-0230858 A1, filed Mar. 11, 2010. The compliant material can have a Shore A hardness of from about 30 to about 80 durometer. The thickness of the compliant material covering the rigid material will typically be no greater than about 26 mm, from about 1 mm to about 26 mm, or from about 1 mm to about 7 mm.

In an embodiment, the apparatus 36 can include a pressure hood 38. A gap 44 between the pressure hood 38 adjacent the precursor web 34, which is fed between the pressure hood 38 and the forming structure 10, defines the static gas pressure plenum 40. The static gas pressure plenum 40 is utilized to provide a force against a precursor web 34 to force the precursor web 34 into the apertures or depressions, and/or to conform the precursor web to the discrete protruded elements, of the forming structure 10. The gap 44 between the pressure hood 38 and the forming structure 10 can be from about 0.5 mm to about 50 mm or from about 1 mm to about 4 mm. The pressure hood 38 can include at least one high pressure gas inlet 42 allowing high pressure gas to enter the gap 44 between the pressure hood 38 and the forming structure 10 creating the static pressure conditions in the gap 44 between the pressure hood 38 and the forming structure 10.

In an embodiment, the sealing plate 60 maintains a lateral seal against the edges of the forming structure roll 10 and the pressure hood 38.

In an embodiment, the pressure hood 38 is wider than the precursor web 34, which can enhance the seal formed with the pressure hood 38. The pressure differential is sufficient to force the precursor web 34 into the apertures or depressions, or to conform the precursor web 34 to the discrete protruded elements, of the forming structure 10. The pressure differential can be enhanced, for example, by applying a vacuum on the forming structure 10 facing surface of the precursor web 34.

In an embodiment, the static gas pressure plenum 40 may be defined by a high pressure zone 46 created between one or more forming structures 10 and one or more compliant rolls 80. The volume of the high pressure zone 46 created between the one or more forming structures 10 and one or more compliant rolls 80 can vary according to the diameter of the forming structures 10 and compliant rolls 80. Any suitable number of forming structures 10 can be used, such as, for example, one, two, three, four, five, six, eight, ten. Any suitable number of compliant rolls 80 can be used, such as, for example, one, two, three, four, five, six, eight, ten. The total number of forming rolls 10 and compliant rolls 80 should be an even number greater than or equal to four.

In an embodiment, the static gas pressure plenum 40 defined by the one or more forming structures 10 and one or more compliant rolls 80 can provide force against one or more than one forming structure 10 simultaneously. An embodiment with multiple forming structures 10 and one or more compliant rolls 80 can allow for multiple embossings on the same web using the same static gas pressure plenum 40. An embodiment with multiple forming structures 10 and one or more compliant rolls 80 can have variations in the forming structure, such as, for example, the material from which the individual forming structures 10 are made, forming different shapes, different sizes, different area densities, and/or embossing patterns created by the discrete apertures, discrete depressions, discrete protruded elements or combinations thereof of the individual forming structure 10.

In an embodiment, defined by the one or more forming structures 10 and one or more compliant rolls 80, the embodiment can have different static gas pressure plenums 40. The one or more forming structures 10 and the one or more compliant rolls 80 in contact create two or more separate high pressure zones 46 each defining a different the static gas pressure plenum 40.

Each static gas pressure plenum 40 can provide force against one ore more than one forming structure 10 in the high pressure zone 46 simultaneously. An embodiment with multiple forming structures 10 and one or more compliant rolls 80 can allow for multiple embossings on the same web using different static gas pressure plenums 40.

The static gas pressure plenum 40 of an embodiment defined by one or more forming structures 10 and one or more compliant rolls 80 can be affected by aspects of the rolls, such as, for example, the diameter of the compliant rolls 80.

In an embodiment, more than one sealing plate 60 serves to maintain the static gas pressure plenum in the high pressure zone 46.

The apparatus 36 can include a sealing framing plate 62 disposed on each end of the apparatus 36. The framing plate 62 can include the more than one sealing plate 60 in an embodiment comprising one or more forming structures 10 and one or more compliant rolls 80.

In an embodiment, the framing plate 62 includes the high pressure gas inlet 42.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for embossing a web comprising:
   one or more compliant rolls;
   one or more forming structures;
   a first sealing framing plate on a first end of the apparatus; and
   a second sealing framing plate on a second end of the apparatus;
   wherein the one or more forming structures and the one or more compliant rolls are in contact forming a high pressure zone defining a static gas pressure plenum;
   wherein said static gas pressure plenum provides a static gas pressure of from about 1 MPa to about 25 MPa;
   wherein each forming structure contacts two compliant rolls;
   wherein the total number of forming structures and compliant rolls is an even number greater than or equal to four;
   wherein the first sealing framing plate and the second sealing framing plate comprises of one or more sealing plates; and
   wherein one of the first sealing framing plate or the second sealing framing plate comprises a high pressure gas inlet.

2. The apparatus of claim 1, wherein said static gas pressure plenum is defined by contacting at least four in total of one or more of said forming structures with the one or more said compliant rolls.

3. The apparatus of claim 1, wherein the one or more forming structures and the one or more compliant rolls in contact create two or more separate high pressure zones each defining a different said gas pressure plenum.

4. The apparatus of claim 1, wherein the one or more forming structures comprises a vacuum within a forming structure.

5. The apparatus of claim 1, wherein the one or more forming structures comprise protruded elements.

6. The apparatus of claim 1, wherein said apparatus further comprises an infeed idler roll and an outfeed idler roll, wherein the infeed idler roller and the outfeed idler roller are adjustable in relation to the forming structures.

7. The apparatus of claim 6, wherein said infeed sealing roller and said outfeed sealing roller each comprise a compliant material, wherein the compliant material is a material having a Shore A hardness between 30 and 80 durometer.

\* \* \* \* \*